US005702019A

United States Patent [19]

Grimard

[11] Patent Number: 5,702,019

[45] Date of Patent: Dec. 30, 1997

[54] VIAL HAVING RESEALABLE MEMBRANE ASSEMBLY ACTIVATED BY A MEDICAL DELIVERY DEVICE

[75] Inventor: Jean Pierre Grimard, Vif, France

[73] Assignee: Becton Dickinson France S.A., LePont de Claix, France

[21] Appl. No.: 534,754

[22] Filed: Sep. 27, 1995

[51] Int. Cl.$^6$ .......................... A61M 37/00; B65D 41/50; B65D 45/30

[52] U.S. Cl. .......................... 215/301; 141/24; 141/319; 141/349; 141/383; 215/274; 215/302; 215/307; 215/DIG. 3; 220/203.11; 604/91

[58] Field of Search .......................... 215/301, 299, 215/307, 310, 231, 329, 270, 275, 302, 350, DIG. 3; 220/367.1, 368, 254, 203.07, 203.11, 203.15–17; 604/411, 412, 413, 414, 415, 416, 89, 90, 91; 128/760; 141/23, 24, 26, 27, 312, 319, 349, 350, 383, 386

[56] References Cited

U.S. PATENT DOCUMENTS

| | | | |
|---|---|---|---|
| 2,607,503 | 8/1952 | Sonnenberg | 215/326 X |
| 2,953,132 | 9/1960 | Richter et al. . | |
| 3,164,303 | 1/1965 | Trautmann | 604/89 X |
| 3,206,080 | 9/1965 | Scislowicz . | |
| 3,356,093 | 12/1967 | Mohahon | 141/349 |
| 3,357,427 | 12/1967 | Wittke et al. | 141/27 X |
| 3,674,028 | 7/1972 | Ogle . | |
| 3,779,371 | 12/1973 | Rovinski | 604/90 X |
| 3,838,689 | 10/1974 | Cohen | 604/90 |
| 4,210,255 | 7/1980 | Pan | 220/203.15 |
| 4,672,996 | 6/1987 | Floyd et al. | 220/203.11 X |
| 4,822,351 | 4/1989 | Purcell . | |
| 5,291,991 | 3/1994 | Meyer . | |
| 5,348,548 | 9/1994 | Meyer et al. . | |
| 5,352,196 | 10/1994 | Haber et al. | 604/90 |
| 5,358,501 | 10/1994 | Meyer . | |
| 5,360,413 | 11/1994 | Leason et al. . | |
| 5,423,791 | 6/1995 | Bartlett . | |
| 5,425,465 | 6/1995 | Healy . | |
| 5,494,170 | 2/1996 | Burns | 215/249 X |

FOREIGN PATENT DOCUMENTS

| | | |
|---|---|---|
| 0 406 374 B1 | 12/1990 | European Pat. Off. . |
| 1071487 | 3/1954 | France . |
| 1487413 | 5/1967 | France . |
| 3618158A1 | 3/1987 | Germany . |
| 501 172 | 2/1971 | Switzerland . |
| WO 95/3841 | 2/1995 | WIPO . |

*Primary Examiner*—Allan N. Shoap
*Assistant Examiner*—Naki M. Kopsidas
*Attorney, Agent, or Firm*—Vincent A. Castiglione

[57] ABSTRACT

A resealable assembly for a container such as a bottle or vial featuring a membrane for selectively opening or sealing a fluid path between the bottle and a medical delivery device introduced into the assembly. The assembly includes a body disposed on said bottle, and a luer connector hub which may be separately provided with the body or formed integrally therewith. The luer connector hub features a connector end open for access by the medical delivery device, and an opposed end which is disposed for fluid communication with the open top of the bottle. A membrane, preferably formed from an elastomeric material, is secured across both the opposed end of the luer connector hub and the open top of the bottle, and may be retained between the top surface of the bottle and the body. The membrane preferably includes a central area sealing the opposed end of the luer connector hub from the open top of the bottle, with one or more fluid openings defined on a portion of the membrane outside of the central area. A force exerted on the central area by the medical delivery device deflects the membrane towards the interior of the vial, urging the membrane from sealing contact with the body and, hence, opening the fluid path between the interior of the bottle and the medical delivery device. The central area may display one or more fluid flow channels to facilitate fluid flow between the medical delivery device and the bottle as contact is made between the medical delivery device and the central area of the membrane. A sealing rib may be provided around a portion of the periphery of the luer connector hub to enhance sealing contact between the membrane and the luer connector hub.

25 Claims, 14 Drawing Sheets

VIAL HAVING RESEALABLE MEMBRANE ASSEMBLY ACTIVATED BY A MEDICAL DELIVERY DEVICE

FIELD OF THE INVENTION

The invention relates to a vial having a resealable membrane assembly, and more particularly, to a vial having a resealable membrane assembly activated by a medical delivery device for efficient transfer of fluid to or from the vial.

BACKGROUND

Dry drugs such as powdered or lyophilized drugs are typically stored in sealed vials. In practice, the drug is accessed shortly prior to use by rupturing or piercing the seal. A solvent solution such as saline is then introduced into the vial to reconstitute the powdered or lyophilized drug. Once reconstituted, the drug solution is extracted from the vial for use.

Some prior art vials of powdered or lyophilized drugs include a pierceable membrane secured across the open top of the prior art vial. The membrane is normally pierced by a needle in communication with the solvent. However, care must be taken to avoid the separation of membrane fragments when the seal is pierced, as these may be accidentally delivered to the patient. Typically, these seals must be pierced each time access to the solvent is desired, heightening the problems associated therewith.

Other prior art vials include rubber stoppers that are either removed from or urged into the vial when delivering the solvent for reconstituting the drug. While in general these assemblies work well to safely store the drug prior to use, one drawback of these stoppers is that they cannot be accessed after they have fallen into the vial. Hence, the vial cannot be reseated employing the stopper originally provided. Accordingly, the structure of these prior art vials is not readily adapted to a vial capable of repeated opening or closing. Where a practitioner may not desire or need to administer the entire dose of reconstituted drug held in the vial, the vial would typically need to be resealed against the ambient environment to preserve the sterility of the drug remaining in the vial.

The stopper employed with a particular drug is typically formulated from a material compatible with the drug held in the vial. While the stopper normally poses no harm to the safety of the reconstituted drug, there may be a perception—however flawed—that the presence of the stopper in the interior of the vial somehow adversely affects the drug held therein. Also, there may be the perception that the presence of the stopper in the vial may interfere with the subsequent flow of the drug solution.

SUMMARY OF THE INVENTION

A resealable assembly for a vial or bottle is provided for resealable fluid access to and from the interior of the vial or bottle. The assembly establishes a resealable fluid path between a medical delivery device for introducing into, or aspirating out of the bottle, fluids, and permits a practitioner repeated access to the drug held in the bottle while at the same time preserving its sterility.

The bottle includes an interior, an open top in fluid communication with the interior, and a top surface disposed around portions of the bottle surrounding the open top. The top surface may be formed, for instance, as an annular rim around the open top.

The resealable assembly features a body disposed on the top surface of the bottle. A fluid access device is disposed on the body to provide fluid access to and from the interior of the bottle. In one embodiment, the fluid access device is configured as a luer connector hub. The luer connector hub includes a connector end configured for access by a component of a medical delivery device, and an opposed end disposed for fluid communication with the open top of the bottle. If desired, the body and the luer connector hub may be provided as separate components, or they may be integrally formed as one component.

The connector assembly further includes a membrane disposed between the open top of the bottle and the opposed end of the luer connector hub. The membrane may be supported between the body and the top surface of the bottle. The membrane may be held in place, for instance, by an annular clip retaining the body to the top surface of the bottle. If desired, the body and the top surface of the bottle may be formed as an integral component, with the membrane secured in the integral component so as to be disposed between the opposed end of the luer connector hub and the open top of the bottle.

The membrane, which may be formed from an elastomeric material such as various thermoplastic elastomers, natural or synthetic rubbers, or the like, preferably includes a central area disposed for contact with the medical delivery device introduced into the luer connector hub. The central area also features a width at least equal to the width defined by the opposed end of the luer connector hub. One or more fluid openings are preferably disposed on the membrane outside the central area. The openings form part of the resealable, fluid path between the open top of the bottle and the medical delivery device.

One or more sealing ribs may be disposed on the body about the periphery of the opposed end of the luer connector hub. The sealing ribs preferably are disposed for sealing contact with the membrane in a location between the central area and the one or more openings. If desired, the sealing ribs may be provided on the membrane itself. The membrane is displaceable between a sealing position, wherein the membrane is disposed for sealing contact with the body to close the fluid path, and an open position, wherein the membrane is urged away from the body to open the fluid path. If desired, one or more fluid channels may be defined in the central area of the membrane to facilitate fluid flow between the medical delivery device and the membrane as the membrane is displaced by the medical delivery device into its open position.

If desired, a luer lock seal may be provided which is threadably engageable with the connector end of the luer connector hub. The luer lock seal prevents inadvertent access to the interior of the bottle until use is ultimately desired. Also, if desired, a protective cap may be fitted about the exterior of the bottle to protect the luer connector hub. The cap may be affixed with a tamper-evident seal, as is conventional.

In use, the luer lock seal (if provided) is removed by the practitioner, so that the connector end of the luer connector hub is disposed for access by the medical delivery device. The medical delivery device may feature a male luer tip which is insertable through the connector end of the luer connector hub. The male luer tip will exert a force against the central area of the membrane, such that the membrane will be displaced into its open position. The membrane will be displaced from its sealing contact with the sealing ribs, thereby creating a gap between the membrane and the sealing ribs. Fluid flow is thereby permitted between the medical delivery device and the interior of the bottle via the one or more channels formed in the central area of the membrane and, via the one or more openings in the membrane, the fluid path between the open top of the bottle and the medical delivery device. Upon removing the medical delivery device from contact with the central area, the membrane will re-deflect towards its closed position, such that the membrane will be redisposed for sealing contact with the fibs, closing the fluid path.

BRIEF DESCRIPTION OF THE DRAWINGS

The invention will now be described in greater detail by way of reference to the appended drawings, wherein.

DETAILED DESCRIPTION OF THE PREFERRED EMBODIMENTS

While the description and figures herein makes reference to a vial or bottle, it will be understood and appreciated by the skilled artisan that any type of container normally employed in the field of endeavor, such as capsules, jars or like vessels are readily amenable to the advantages described herein. In addition, while herein described with regard to containers having a quantity of dry drug or medicament for reconstitution by liquid obtained from an external source, it will be appreciated by the skilled artisan that the invention is not so limited. For instance, the invention may be applied to containers holding therein a quantity of liquid medication, wherein repeated access is desired.

Figure 1:
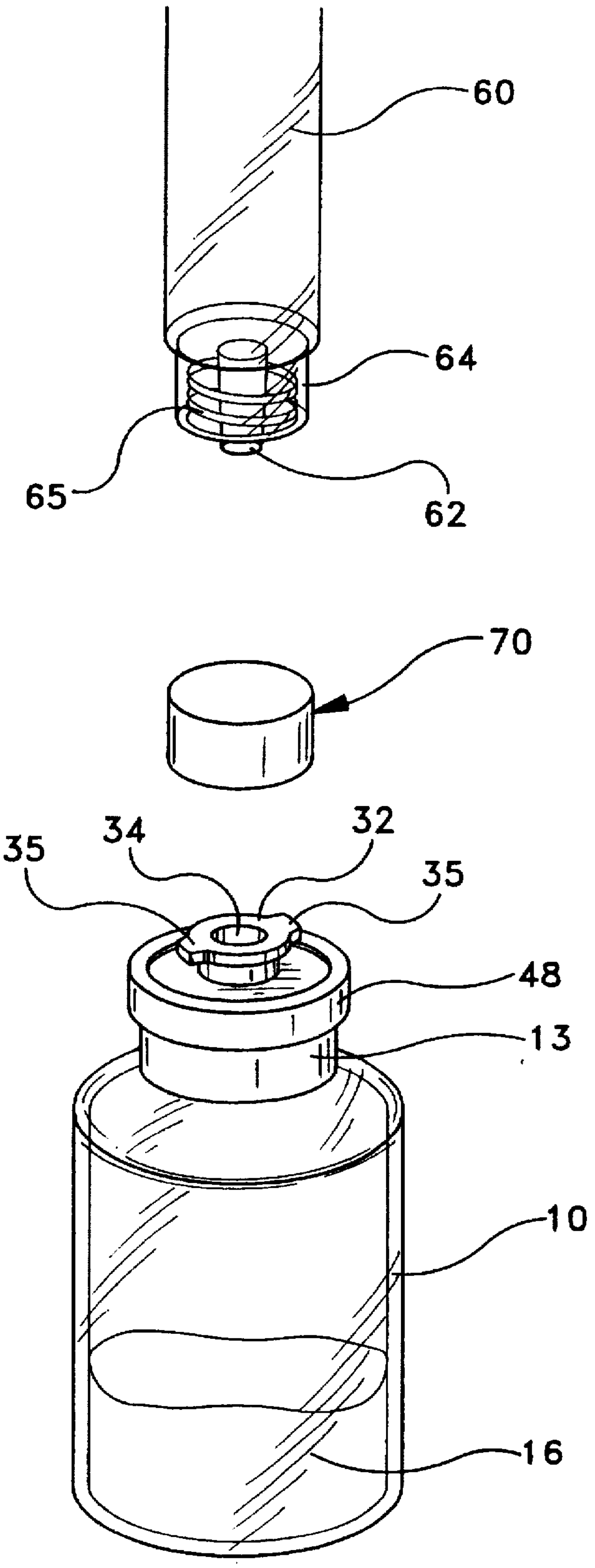
FIG. 1 is a blow-up view in perspective of a resealable bottle assembly affixed to a bottle containing therein a drug, with a medical delivery device such as a a syringe employed to deliver to the drug.

Turning now to the drawings, wherein like numerals depict like components, FIGS. 2–10 depict an embodiment 20 of a resealable bottle assembly in accordance with the present invention, and FIG. 1 is an exploded perspective view of resealable bottle assembly 20 mounted to a bottle or vial 10 containing therein a drug 16. Drug 16 may entail, for instance, a medicament in powdered or granular form, such as a lyophilized medicament, intended to be reconstituted by a fluid introduced into vial 10 by a medical delivery device such as syringe 60. Alternately, it will be appreciated by the skilled artisan that drug 16 may entail a fully liquid medicament to which repeated access by the practitioner is desired.

Syringe 60 may feature, for instance, a male luer tip 62 for introducing fluid into the interior of bottle 10 via a luer connector hub 32 associated with the resealable bottle assembly 20, as will be more fully described herein. Syringe 60 may also display a luer lock collar 64 surrounding luer tip 62. Internal portions of luer lock collar 64 may include a thread 65 engageable with an edge 35 associated with luer connector hub 32. While syringe 60 is herein depicted as a luer lock syringe, it will be evident to the skilled artisan that the invention is equally amenable to luer slip syringes. It will also be evident to the skilled artisan that syringe 60 may serve to aspirate reconstituted drug 16 from bottle 10.

As will be evident from the various drawings, bottle 10 may include a neck portion 13 defining an open top 12 with a width “X”. Bottle 10 further preferably includes a top surface 14 disposed around open top 12. In the configuration depicted herein, top surface 14 is defined by an uppermost portion of an annular rim 15 formed around open top 12 of the bottle. It will be realized by the skilled artisan that the top surface of the bottle may also be established by rings or other means attached about open top 12 of the bottle.

Turning now to FIGS. 2–10, resealable bottle assembly 20 features a relatively flat body 22. Body 22 may be formed separate from bottle 10, and attached to top surface 14 of the bottle by securing the body to annular rim 15 with a crimp cap 48. It will also be evident to the skilled artisan that in lieu of a body separately supplied, body 22 may be unitarily formed with bottle 10. For instance, body 22 may define a contiguous extension of annular rim 15.

Resealable bottle assembly 20 includes means for communicating with bottle 10, fluids either supplied by a medical delivery device such as syringe 60 or which will be aspirated out of bottle 10. Such means for communicating may take many forms, and need not be restricted to any one type of structure. For example, the means for communicating fluids can be formed as a needle transfer assembly as taught, for instance, in U.S. Pat. No. 5,358,501. As here depicted, the means for communicating fluids is provided as a luer connector hub 32. Other means will be envisioned by the skilled artisan.

Figure 2:
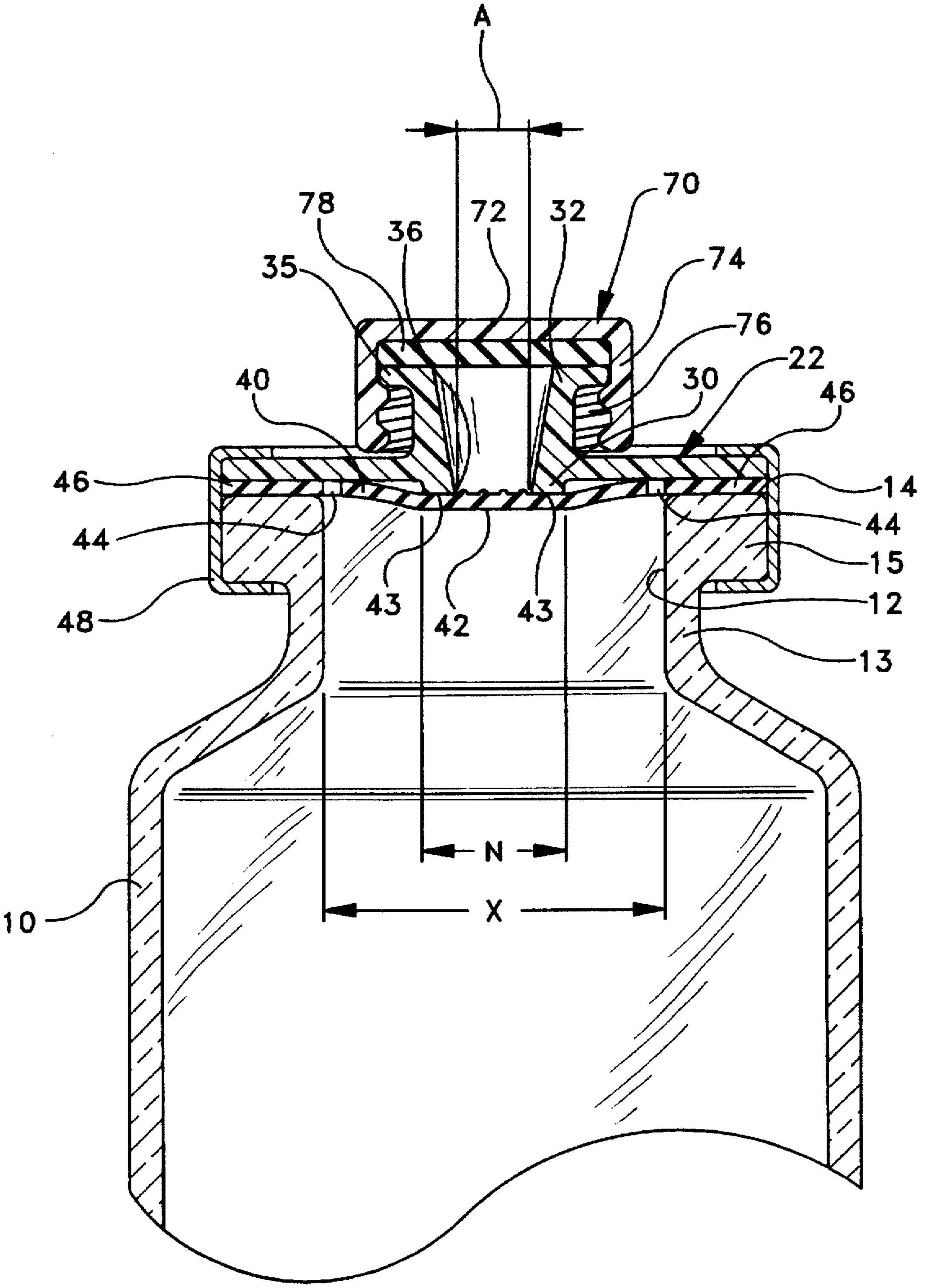
FIG. 2 is a cut-away view depicting one embodiment of a resealable bottle assembly in accordance with the present invention.
Figure 3:
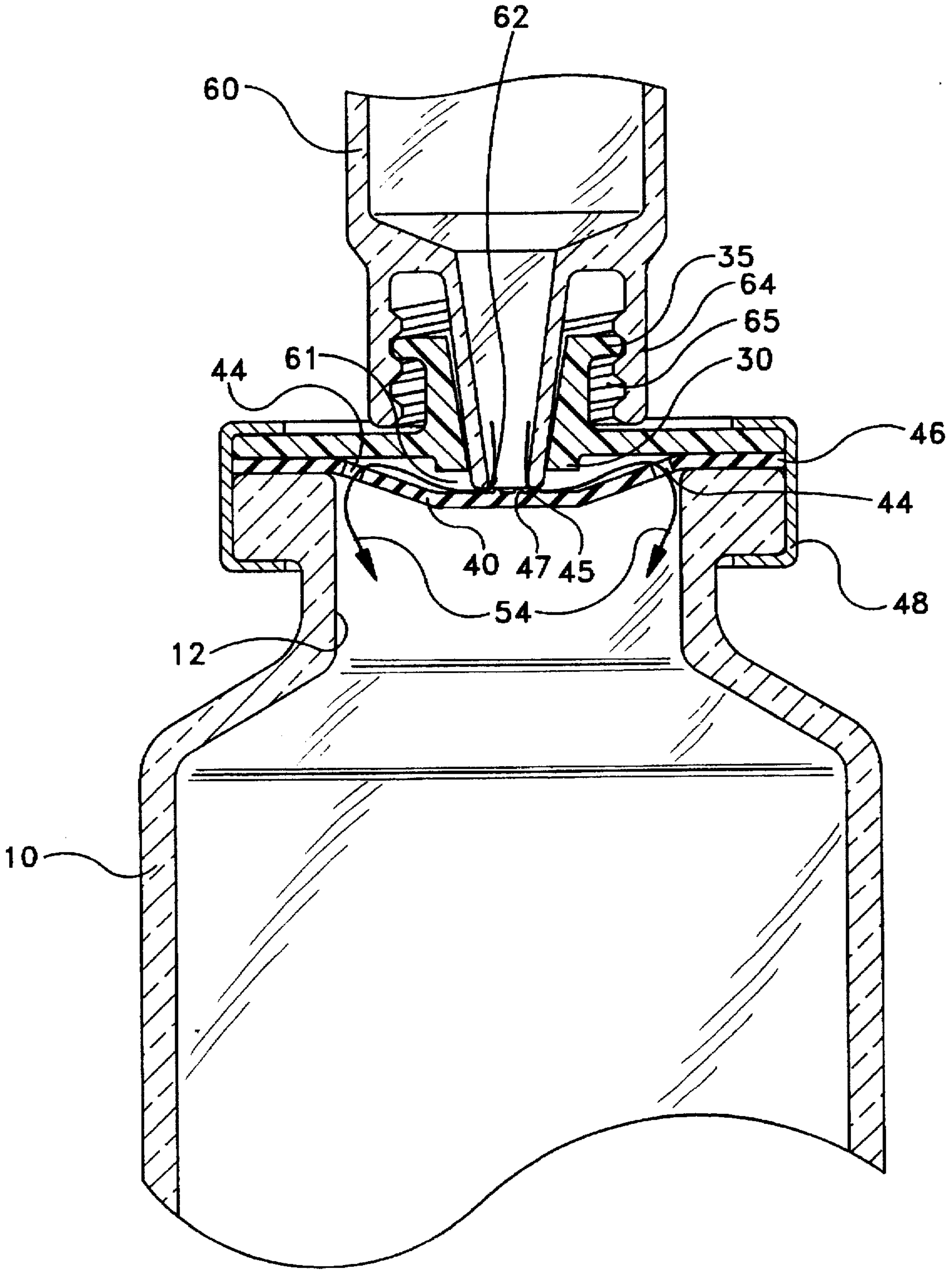
FIG. 3 is another cut-away view of the resealable bottle assembly of FIG. 2, illustrating displacement of the membrane to its open position by action of the medical delivery device, thereby opening the fluid path between the medical delivery device and the open top of the bottle.

The luer connector hub features a connector end 34 configured for access by luer tip 62 of the syringe, and an opposed end 36 located on body 22 adjacent open top 12 of the bottle. As illustrated in FIG. 2, opposed end 36 of the luer connector hub may define a width “A” less than the width “X” of open top 12 of the bottle. For purposes which will be hereinafter more fully described, a sealing rib 30 is preferably provided about the periphery of opposed end 36 of the luer connector hub. Sealing rib 30 may be formed as part of body 22, or it can form an extension of opposed end 36 of luer connector hub 32.

It will be apparent to the skilled artisan that luer connector hub 32 may be supplied separately from body 22 and affixed thereto, for instance, by adhesives, welding, or like affixation methods. Likewise, it will be realized by the skilled artisan that, if desired, luer connector hub 32 may be unitarily formed with body 22.

Resealable bottle assembly 20 preferably features a membrane 40 which is displaceable between an open position (FIGS. 3, 6, 7) and a closed position (FIGS. 2, 4) relative to body 22. As will be herein described, when the membrane is disposed in its open position, a fluid path 54 is established between luer tip 62 and open top 12 of the bottle, permitting free fluid flow between syringe 60 and the interior of bottle 10. Likewise, fluid path 54 is closed when membrane 40 is returned to its closed position, preventing fluid flow through luer connector hub 32, and isolating the interior of bottle 10 from the ambient environment.

As depicted in FIGS. 2–7, membrane 40, which may be formed from an elastomeric material such as various thermoplastic elastomers, natural or synthetic rubbers, or the like, can be configured in a roughly cylindrical, planar manner. Membrane 40 includes an edge 46 securable between body 22 and top surface 14 of the bottle, for instance, by the force exerted by crimp cap 48. Membrane 40 preferably includes a central area 42 having a width "N" at least equal to width "A" of opposed end 36 of the luer connector hub. Membrane 40 is actuated into its open position (FIGS. 3, 6, 7) when luer tip 62 is inserted through open end 34 of the luer connector hub for contact with central area 42 of the membrane. Thus, when the membrane is secured to bottle 10, central area 42 is disposed fully across the opposed end of luer connector hub 32.

Figure 12A:
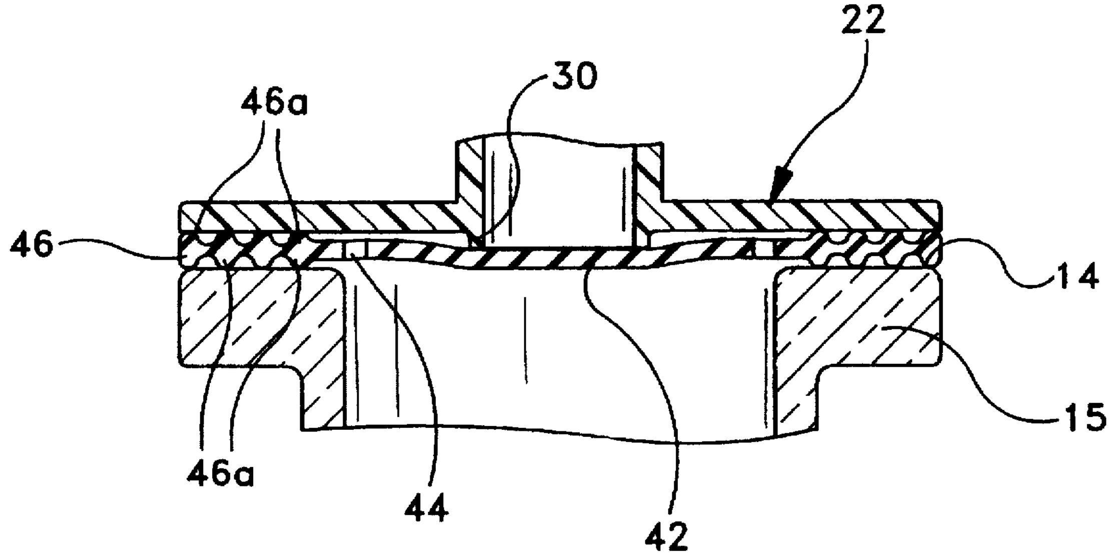
FIGS. 12*a*–12*d* depict various structures for enhancing retention of the membrane between the body and the stop surface of the bottle.
Figure 12B:
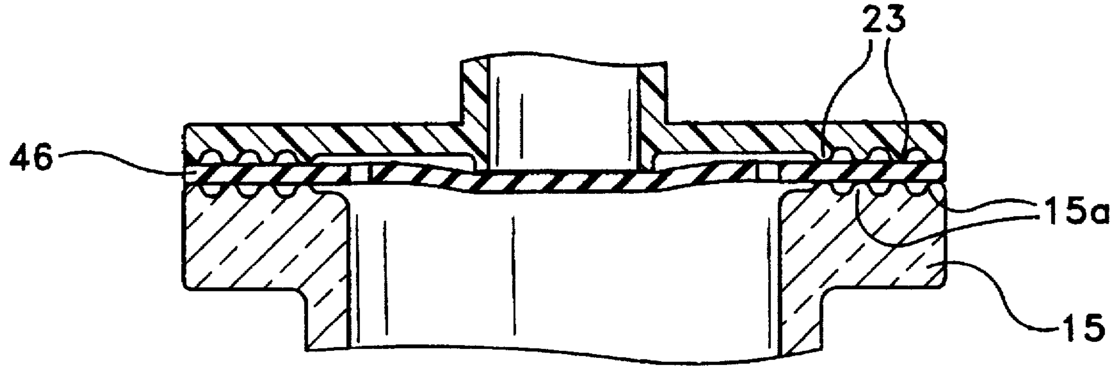
Figure 12C:
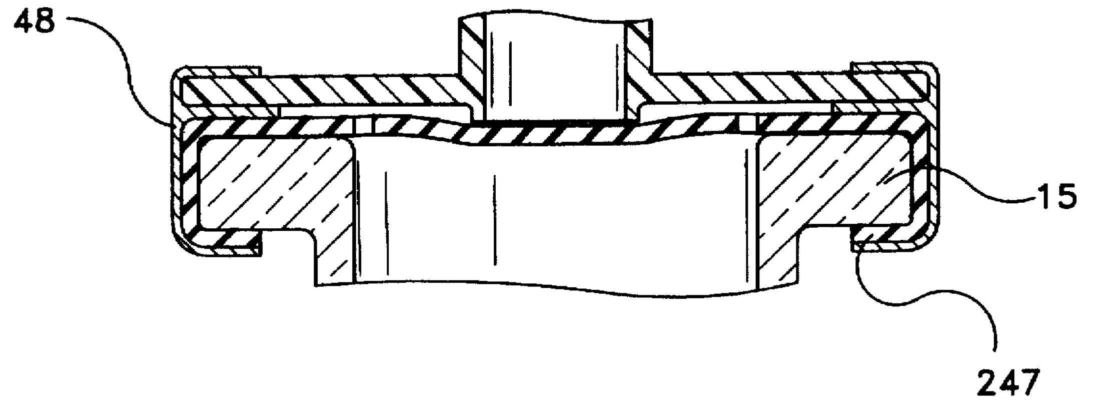
Figure 12D:
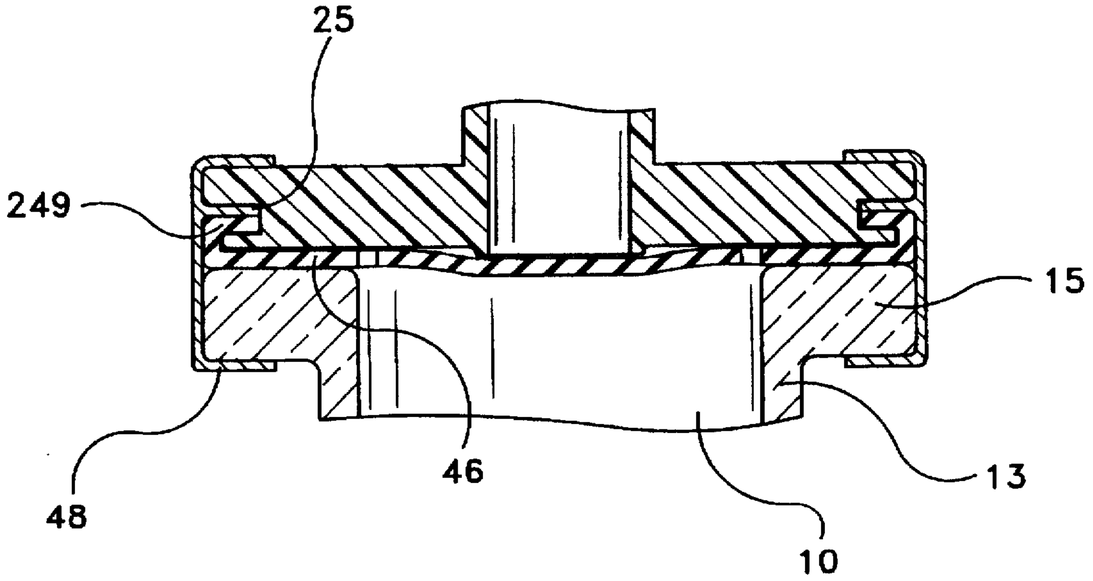

Various structures may be incorporated to assist in the retention of membrane 40 between body 22 and the top surface of the bottle. For instance, ribs 46*a* (FIG. 12*a*) may be incorporated onto edge 46 to provide extra grip between body 22 and annular rim 15. Likewise, ribs 23 and/or ribs 15*a* (FIG. 12*b*) may be incorporated on the body and/or the annular rim, respectively, for the same purpose. Alternately, as seen in FIG. 12*c*, membrane 40 may include a flap 247 which is locked beneath annular rim 15 by the action of crimp cap 48. Likewise, the membrane might include a portion 249 wedged into a slot 25 defined in body 22 (FIG. 12*d*), enhancing the gripping action of the crimp cap. Other variations will be envisioned by the skilled artisan.

Figure 4:
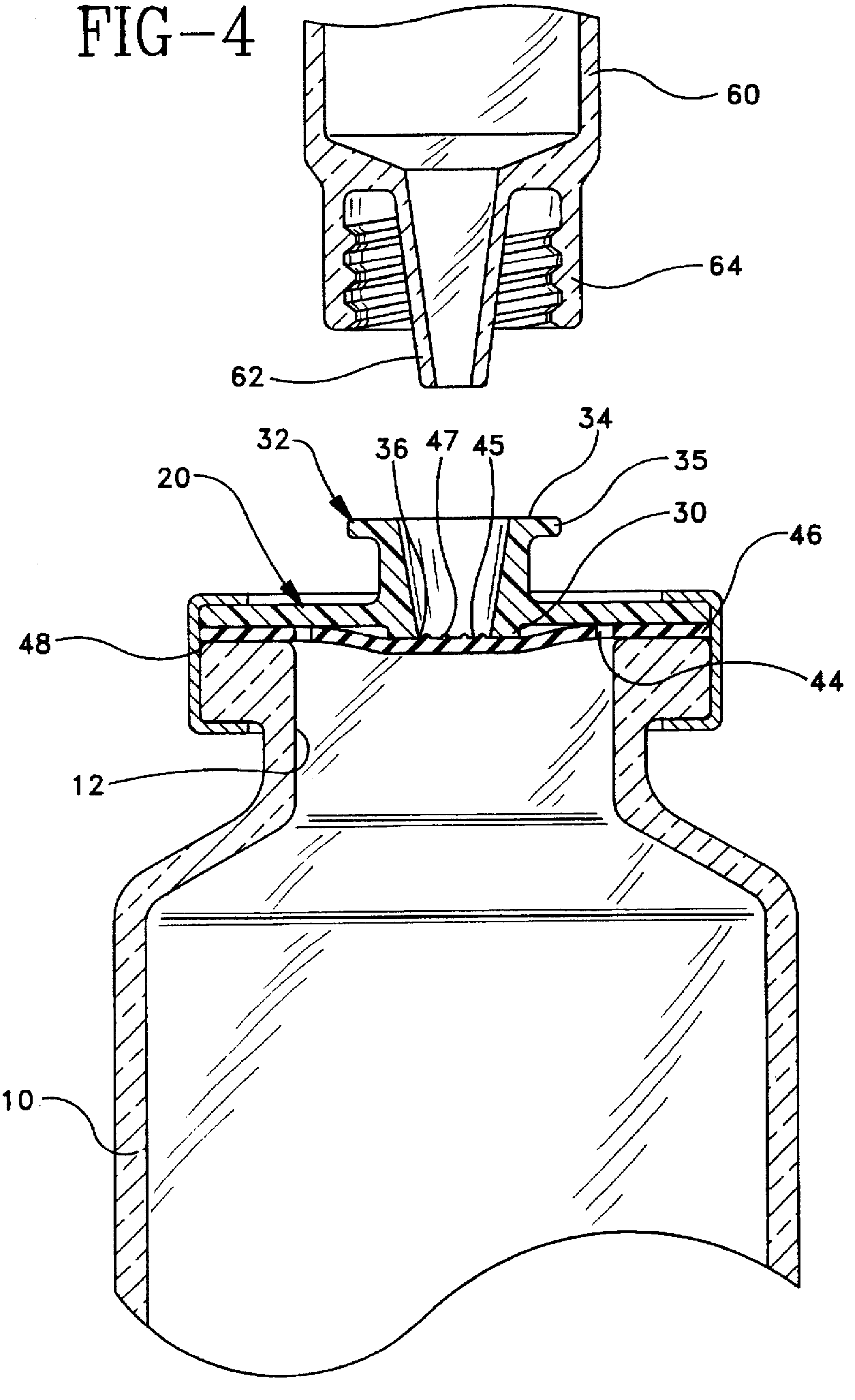
FIG. 4 is another cut-away view of the resealable bottle assembly of FIG. 2, illustrating resealing of the membrane.

Fluid passages are provided on membrane 40 to enable fluid communication between the open top of the bottle and the opposed end of the her connector hub. In one configuration, the fluid passages are configured as one or more openings 44 preferably defined on membrane 40 outside of central area 42. Openings 44 form part of fluid path 54 when membrane 40 is disposed in its open position. The one or more openings 44 are located on membrane 40 such that when the membrane is disposed in its closed position (FIGS. 2 and 4), sealing rib 30 will contact the membrane in a sealing area 43 located around the membrane between central area 42 and the one or more openings, sealing luer connector hub 32 from fluid communication with open top 12 of the bottle, hence closing fluid path 54. It will also be realized that membrane 40 may be designed or otherwise formed from an appropriate material such that when the membrane is in its closed position, the one or more openings 44 will rest flush against body 22 (as is illustrated in FIG. 4), further sealing the luer connector hub from fluid communication with the open top of the bottle.

Figure 5:
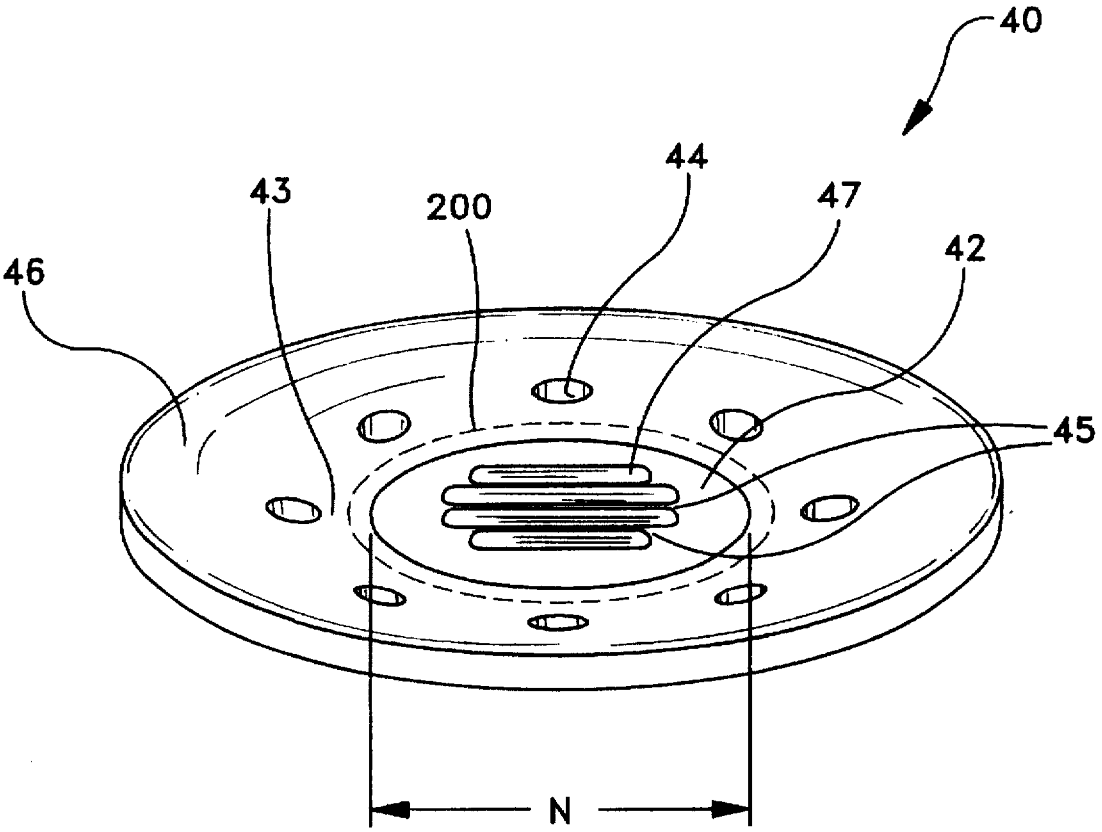
FIG. 5 depicts one embodiment of the membrane illustrated in FIGS. 2–4.
Figure 5A:
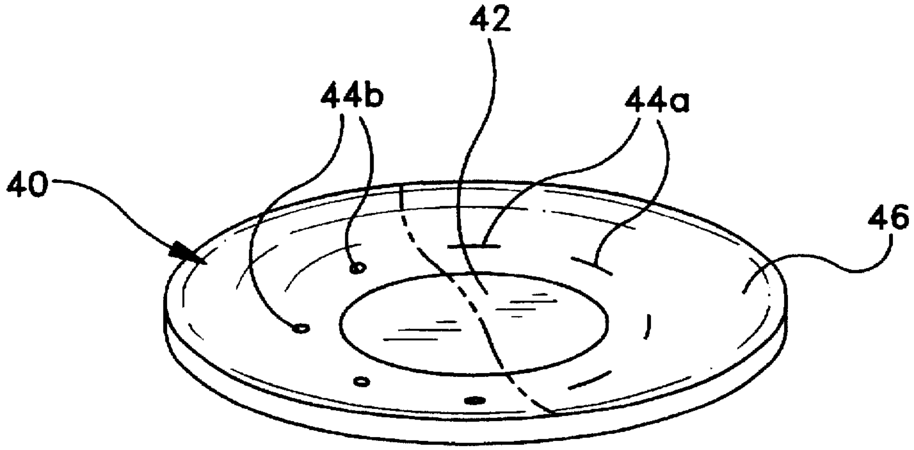
FIG. 5*a* illustrates a variant of the membrane illustrated in FIG. 5.

It will be realized by the skilled artisan that in lieu of openings 44, the fluid passages may be realized as pre-pierced slits 44*a* or pinpoint type punctures 44*b* (See FIG. 5*a*) formed or otherwise provided through membrane 40. Slits 44*a* or punctures 44*b* are configured such that when membrane 40 is disposed in its open position, the slits/punctures will be stretched open to provide fluid access between the open top of the bottle and the luer connector hub. Likewise, when the membrane is disposed in its closed position, slits 44*a* or punctures 44*b* will close, thereby providing a self-sealing ability to enhance the sealing provided by rib 30.

To facilitate fluid flow between luer tip 62 and open top 12 of the bottle, one or more fluid channels 45 may be provided on central area 42. Fluid channels 45, if provided, form part of fluid path 54 openable between luer tip 62 and open top 12 of the bottle. As herein depicted, fluid channels 45 may entail spaces that are defined between ribs 47 formed on the central area. Fluid channels 45 effectively communicate fluid supplied or aspirated via luer tip 62 with portions of membrane 40 outside of central area 42.

Resealable bottle assembly 20 may further include an external seal 70 for preserving the sterility of the various components, inclusive of drug 16, pending use. In one configuration, seal 70 features a circular end wall 72, and a cylindrical side wall 74 with an internal thread 76 configured for threadably engaging edge 35 provided with connector end 34 of the luer connector hub. A suitable sealing material 78, such as a rubber seal, may be secured to the interior face of circular end wall 72. Accordingly, seal 70 can be threadedly engaged onto luer connector hub 32 and tightened such that sealing material 78 sealingly engages open connector end 34 of the luer connector hub. Thus, a barrier is established against the passage of contaminants or other unwanted material through connector end 34 of the luer hub which (if otherwise uncovered), would provide communication through the luer connector hub and, potentially, through open top 12 of bottle 10.

When a practitioner desires to introduce fluid to drug 16 held within bottle 10, luer lock seal 70 may be removed by unscrewing same from connector end 34 of the luer connector hub. Connector end 34 is thus exposed for insertion of luer tip 62 of syringe 60 (see FIGS. 3, 6, 7). By manual force exerted by a user upon syringe 60 or, when structure is provided, by threadedly engaging luer lock collar 64 with edge 35 of the luer connector hub, luer tip 62 is urged into contact against ribs 47 formed on central area 42 of the membrane. It will be seen that luer tip 62 thus urges membrane 40 towards the interior of bottle 10, displacing the membrane to its open position. A gap 61 having a width "C" is created between sealing rib 30 and central area 42. With the opening of gap 61, fluid path 54 is completed between the luer tip and the interior of the bottle 10. Via fluid path 54, fluid flow is fully enabled between syringe 60 and the interior of the bottle via: luer tip 62; fluid channels 45; gap 61; and the one or more openings 44 provided in membrane 40.

A practitioner may now advance a plunger (not shown) associated with syringe 60, thereby supplying fluid to the interior of bottle 10. Thereafter, keeping fluid path 54 open by maintaining the connection between syringe 60 and luer connector hub 32, the practitioner may re-aspirate the now reconstituted drug 16 into syringe 60, causing the reverse fluid flow—i.e., drug 16 may flow into syringe 60 via: the one or openings 44; gap 61; fluid channels 45; and luer tip 62. The drug 16 is thus ready for administration by the practitioner, as desired.

Where it is not desired or necessary to utilize all of drug 16 held within bottle 10, the practitioner may simply reseal bottle 10 by disengaging syringe 60 from luer connector hub 32. As exemplified by FIG. 4, by removing the force exerted by luer tip 62 upon central area 42 of the membrane, membrane 40 will resiliently deflect upwards towards its closed position. Luer connector hub 32 will be sealed from open top 12 of the bottle via sealing engagement between membrane 40 and sealing rib 30. Fluid path 54 will thus be closed, isolating the interior of bottle 10 from exposure with the ambient environment, thereby preserving the sterility of any drug 16 still remaining within the bottle. Also, as previously explained, depending upon the design and resiliency characteristics of membrane 40, openings 44 will also be disposed for contact with body 22, further preventing inadvertent fluid flow between luer connector hub 32 and open top 12 of the bottle, and helping to isolate drug 16 from the ambient environment.

Figure 11A:
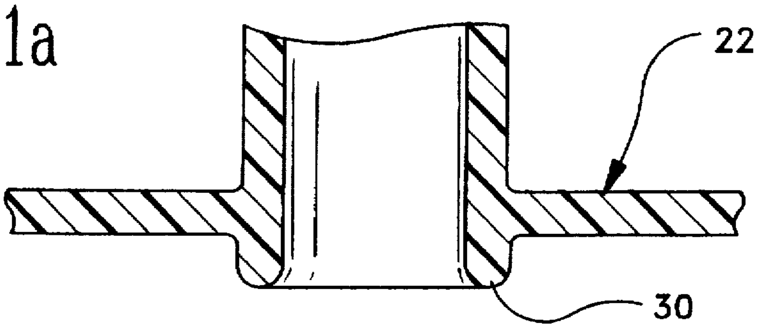
FIGS. 11*a*–11*c* depict various alternative configurations for the sealing rib.
Figure 11B:
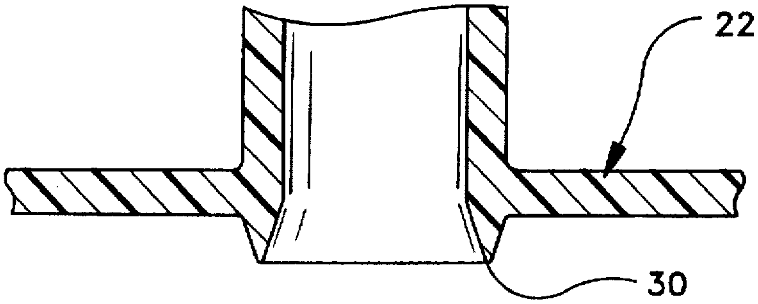
Figure 11C:
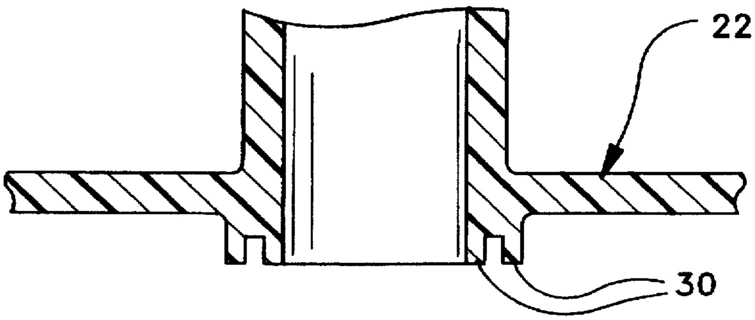

Various features of either of the resealable bottle assembly may be configured in alternate manners. For example, sealing rib 30 is depicted herein with a squared cross-section. However, it will be apparent to the skilled artisan that the sealing ribs may also display a rounded (FIG. 11*a*) cross-sections, peaked or pointed (FIG. 11*b*) cross-sections, or any suitable configuration ensuring sealing contact between rib 30 and membrane 40. Moreover, while for ease of illustration a single sealing rib 30 has been shown, it will be apparent that more than one concentric sealing rib (FIG. 11*c*) may be disposed about the periphery of opposed end 36 of the luer connector hub.

Figure 6:
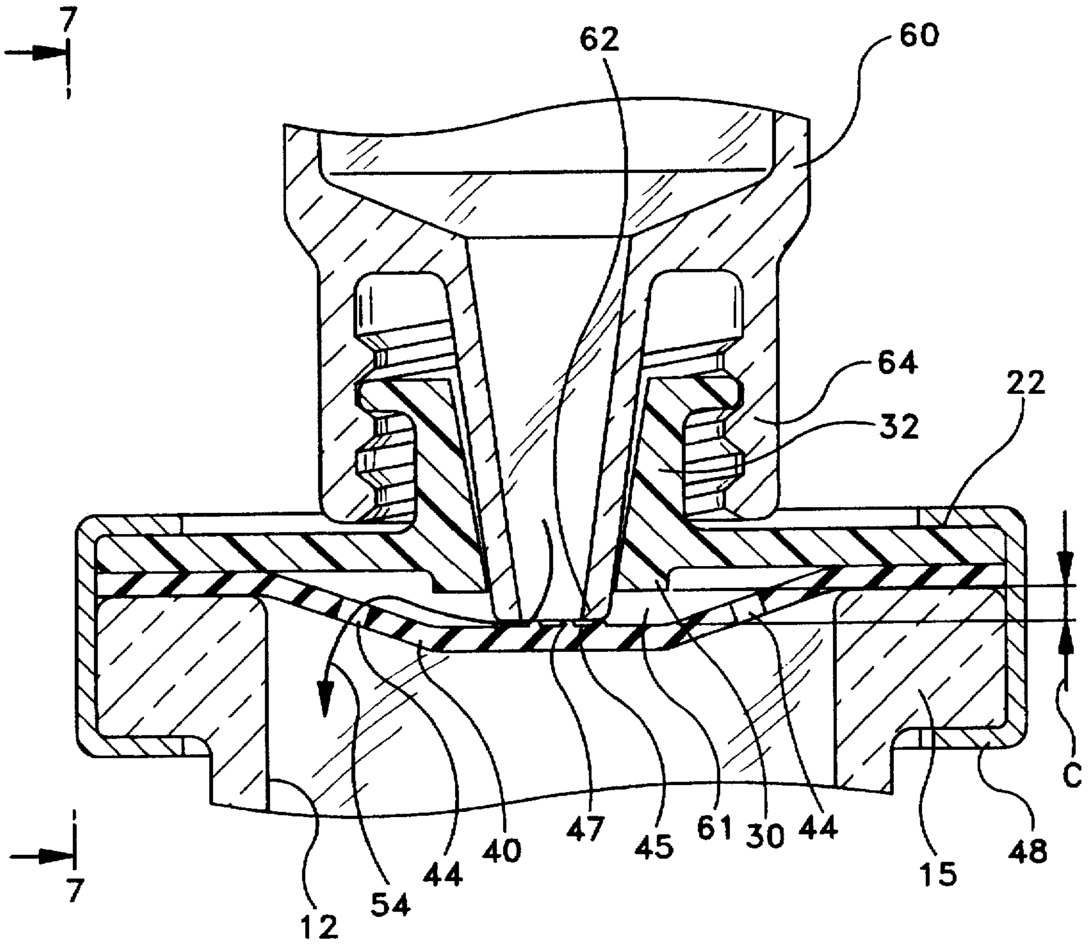
FIG. 6 is a partial cut-away view of the resealable bottle assembly of FIG. 2, illustrating the membrane in its open position and the relationship between the luer tip and the central area of the membrane.
Figure 7:
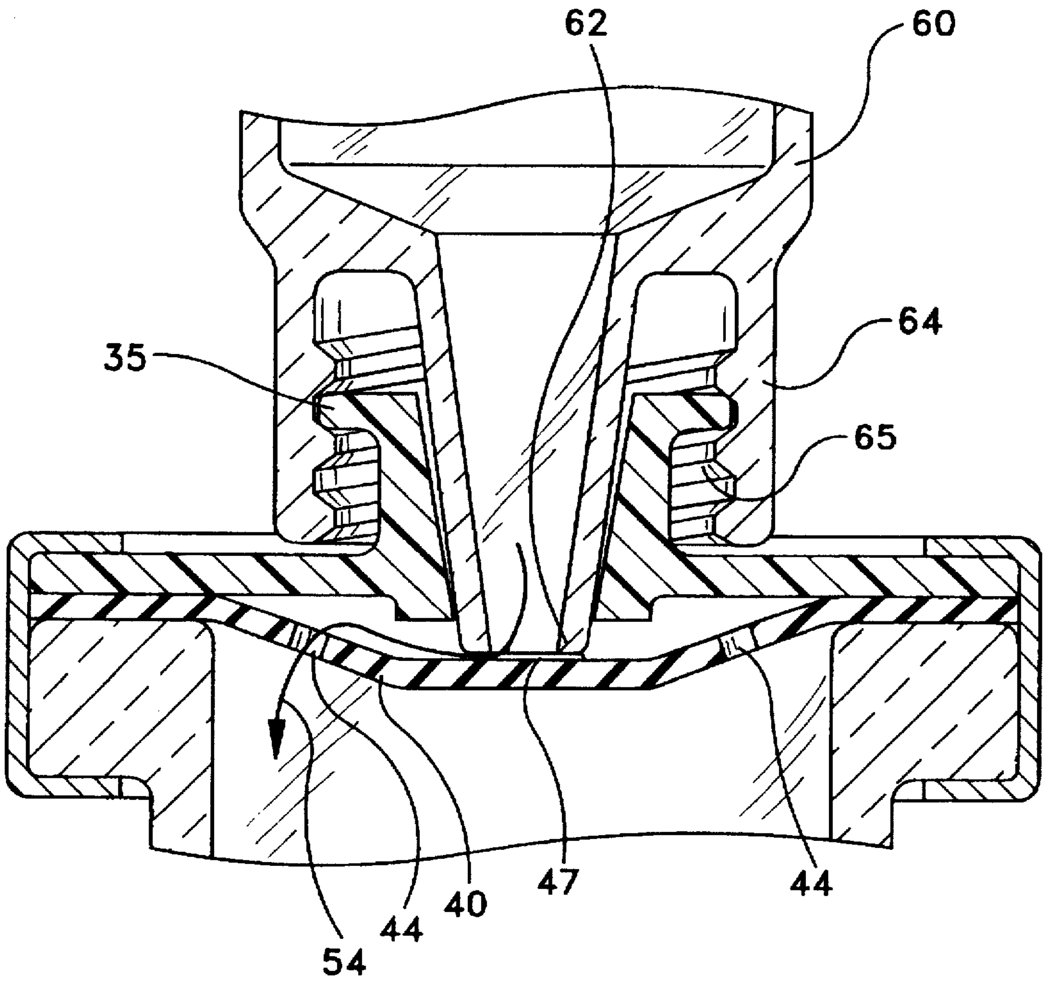
FIG. 7 is another partial cut-away view of the resealable bottle assembly of FIG. 2, as viewed along line 7—7 of FIG. 6.
Figure 8:
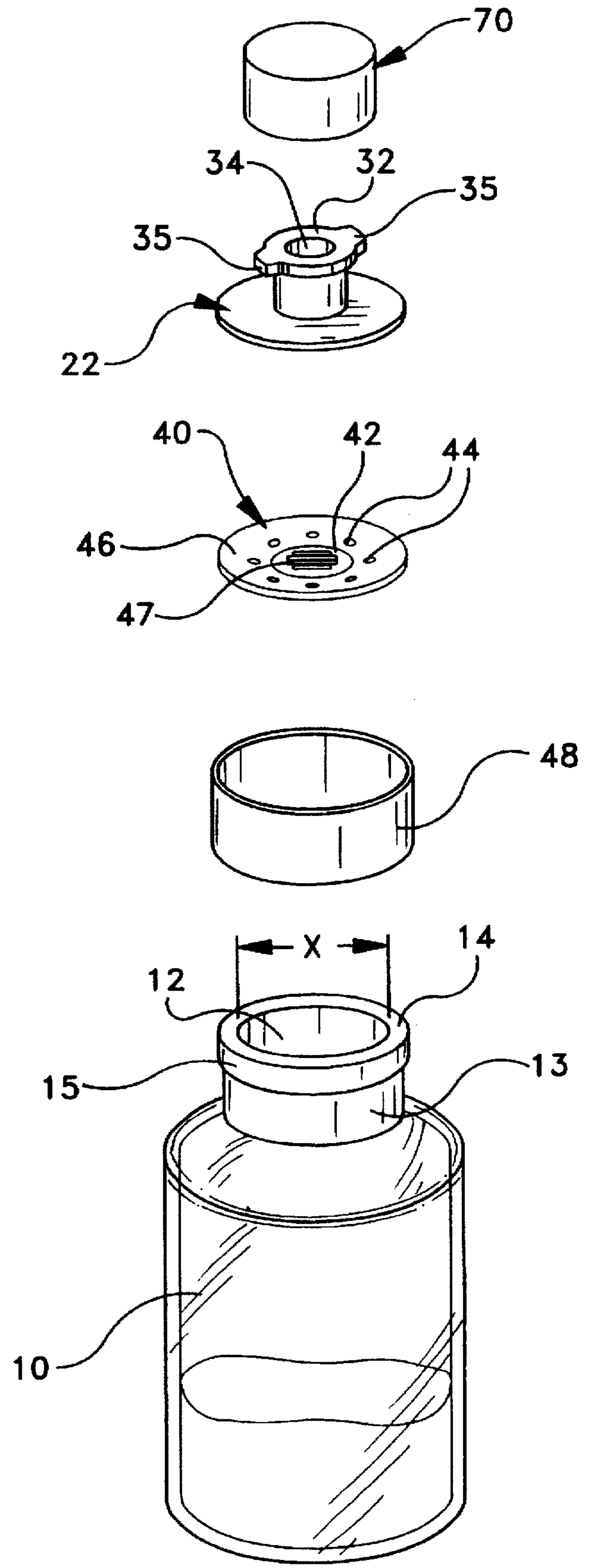
FIG. 8 is an exploded perspective view of the resealable bottle assembly depicted in FIGS. 2–7.

If desired, it will be apparent to the skilled artisan that in lieu of a sealing rib 30 formed with the body or as an extension of the luer connector hub, a sealing rib 200 may be formed as part of the structure of membrane 40 itself (see FIG. 6). Sealing rib 200 may be located between the one or more openings 40 and central area 42. Thus, rib 200 will be urged into sealing contact with body 22 when membrane 40 returns to its closed position.

The various components associated with the luer connector hub, the pusher or the body may be molded or otherwise formed from medical grade plastics, glass, or like materials. Similarly, bottle 10 may be either plastic or glass, as is conventional.

Figure 9:
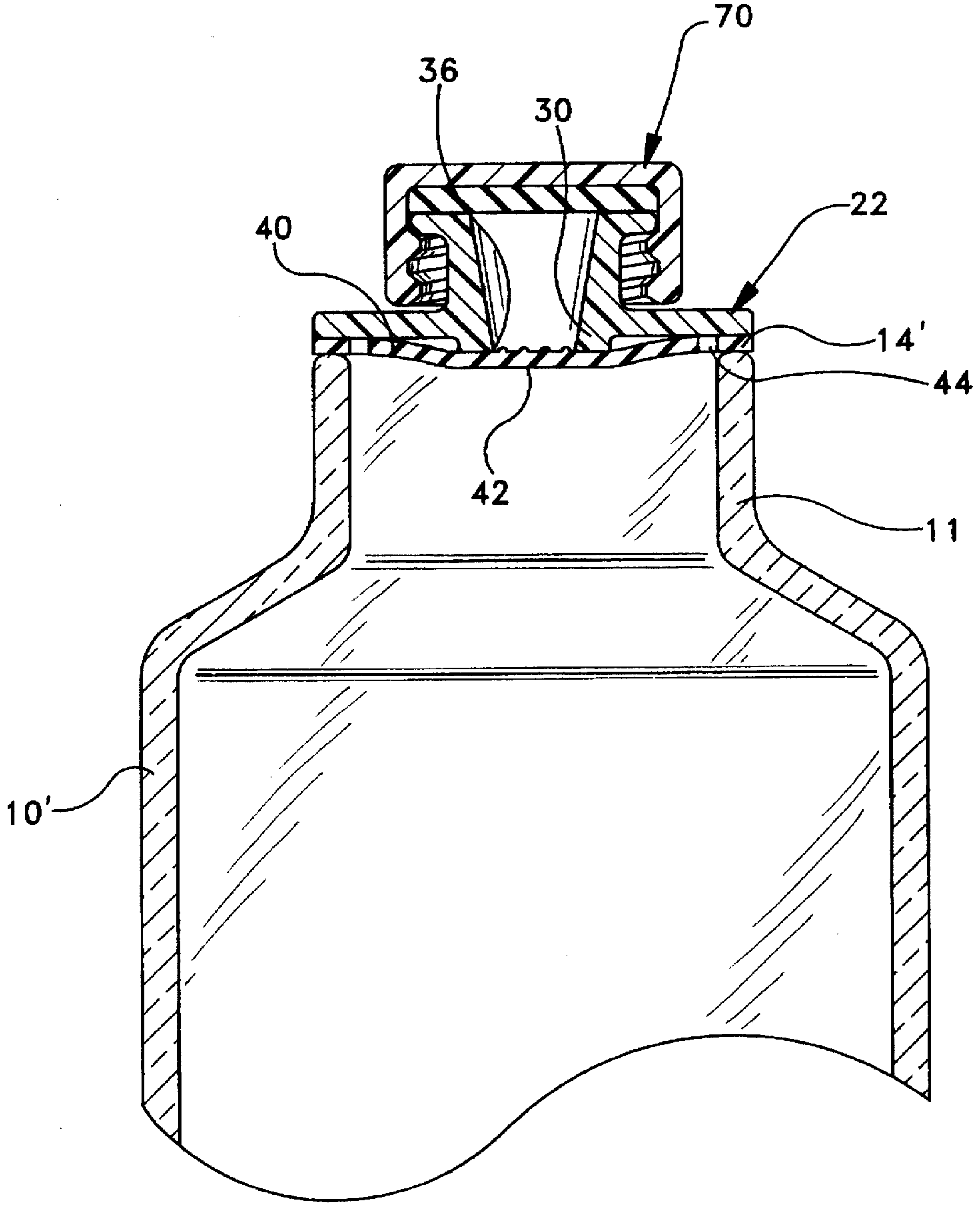
FIG. 9 depicts a rimless bottle employable with the resealable bottle assembly of the present invention.

The principles of the invention are equally applicable to a rimless bottle 10', where a top surface 14' may be encompassed by the uppermost area of wall 11 surrounding open top 12' (see FIG. 9). Here, membrane 40 and body 22 are directly affixed to top surface 14', for instance, by welding, adhesives, or mechanical methods of affixation.

Figure 10:
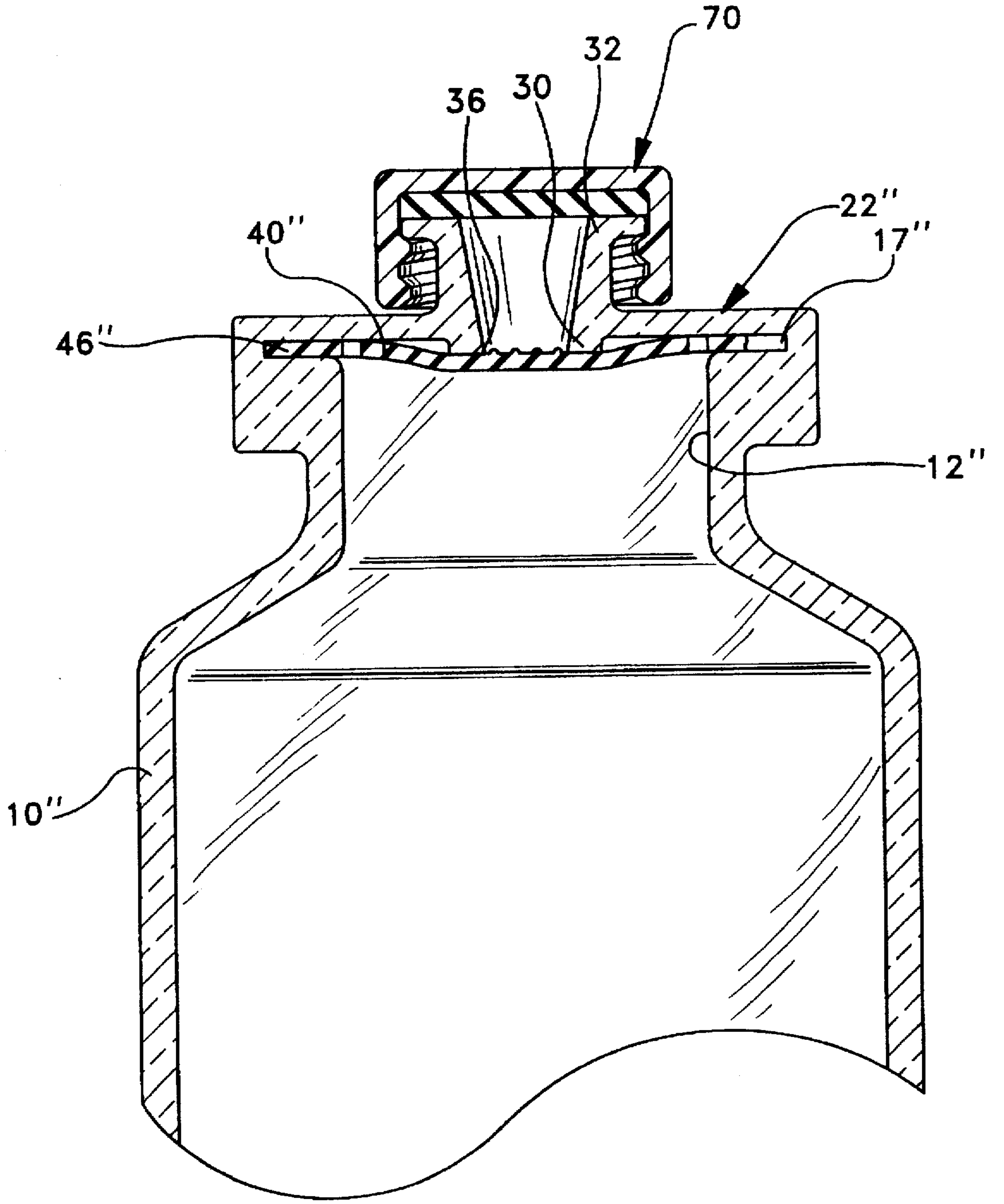
FIG. 10 illustrates unitary manufacture of a body and bottle, and retention of the membrane therein, in accordance with the present invention.

It will also be evident to the skilled artisan that if, as previously described, body 22 and bottle 10 are unitarily formed, membrane 40 may be formed with them, for instance, by a suitable co-injection process. Likewise, as depicted in FIG. 10, if membrane 40 is supplied separately from a unitarily formed bottle 10"/body 22", membrane 40" may be secured across the interface between opposed end 36 of the her connector hub and open top 12" of the bottle, for instance, by supporting edges 46" of membrane 40" in a gap or annulus 17" defined by the unitary bottle 10"/body 22".

Figure 13:
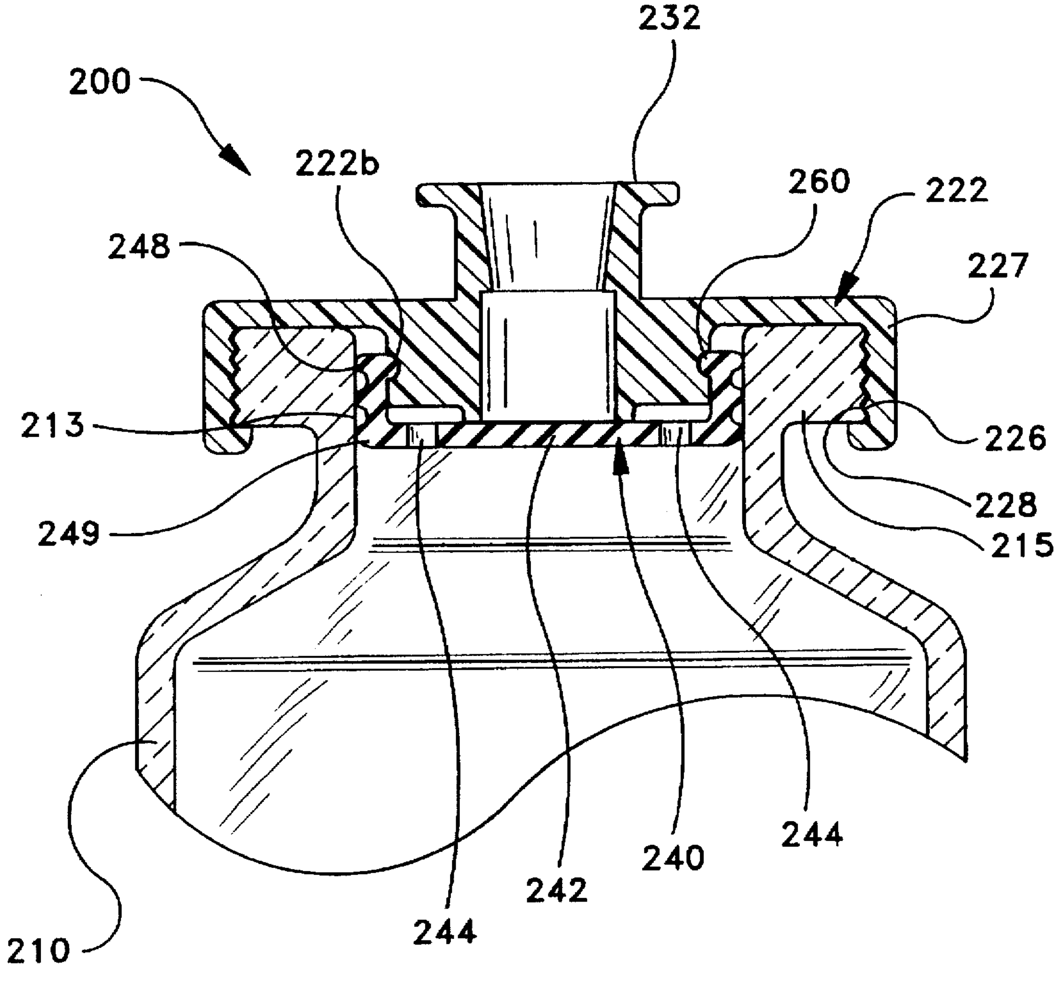
FIG. 13 illustrates an alternate manner of supporting the membrane.

Moreover, it will be realized that the membrane need not be secured between the body and the top surface of the bottle. For instance, the membrane could be associated with the body itself and engaged across the open top of the bottle, for instance, by being secured in the neck of the bottle. FIG. 13 illustrates an embodiment 200 of the resealable bottle assembly substantially as hereinbefore described albeit configured to retain the membrane against the neck of the bottle. A body 222 is provided, having a downwardly extending portion 222*b* that is in fluid communication with a luer connector hub 232 substantially as previously described. Downwardly extending portion 222*b* is configured for insertion into neck portion 213 of bottle 210. Membrane 240 includes an annular bead 248 retained between neck portion 213 and a complementary groove 260 formed on downwardly extending portion 222*b*. One or more annular ribs 249 may also be provided on membrane 240 distal of annular bead 248. While body 222 may be secured to annular rim 215 via a crimp cap, as here shown, body 222 is threadedly secured to annular rim 215 via complementary threads 228, 226 formed on the annular rim and sidewall 227 of the body, respectively. As in the previously described embodiments, membrane 240 rests between the bottom end of luer connector hub 232 (via downwardly extending portion 222*b*) and the open top of the bottle for opening and closing of the fluid path. It will be realized that by this configuration, annular bead 248 and, if provided, the one or more annular ribs 249, may also act as a stopper for bottle 210.

It will be appreciated and understood by those skilled in the art that further and additional forms of the invention may be devised without departing from the spirit and scope of the appended claims, the invention not being limited to the specific embodiments shown.

I claim:

1. A resealable container assembly accessible by a medical delivery device and providing a resealable fluid path between the medical delivery device and the container, comprising:

a container having an open top and a top surface disposed around portions of the container surrounding said open top;

a body disposed adjacent the top surface of the container;

means for communicating fluids with the container, said means having an end configured for introduction of the medical delivery device and an opposed end disposed on said body; and a membrane disposed between the open top of said container and the opposed end of the means for communicating, said membrane having a central area disposed for contact with the medical delivery device and having a width at least equal to the width defined by the opposed end of the means for communicating, said central area comprising at least one fluid flow channel, said membrane having at least one fluid passage located outside said central area for fluid communication, via said at least one fluid flow channel between the medical delivery device introduced into the means for communicating and the open top of the container, and said membrane defining a sealing portion between said central area and said at least one fluid passage for sealing contact with the body, wherein upon contact between said medical delivery device and the central area, said membrane is displaced to an open position, wherein said membrane is urged away from said sealing contact with the body to open the fluid path between the medical delivery device and the container.

2. The reseatable container assembly of claim 1, wherein said means for communicating comprises a luer connector hub.

3. The resealable container assembly of claim 2, further comprising an external seal for sealing the connector end of the luer connector hub.

4. The resealable container assembly of claim 3, wherein said external seal comprises a luer connector seal having a top wall and an annular side wall projecting from said top wall, said annular side wall including an array of internal threads selectively engageable with the connector end of said luer connector hub, and a seal disposed between said top wall and the connector end of the luer connector hub for sealingly engaging said connector end.

5. The resealable container assembly of claim 2, wherein said at least one fluid passage comprises a slit.

6. The resealable container assembly of claim 1 wherein said at least one fluid flow channel comprises spaces defined between raised protrusions provided on said central area.

7. The resealable container assembly of claim 1, wherein said at least one fluid flow channel comprises one or more troughs formed on the surface of the central area.

8. The resealable container assembly of claim 1, further comprising a sealing rib disposed about at least a portion of the periphery of said opposed end of the means for communicating, said sealing rib disposed for said sealing contact with said membrane when said membrane is in the closed position.

9. The resealable container assembly of claim 8, wherein when said medical delivery device displaces said membrane to the open position, said membrane is urged from sealing contact with said sealing rib to create a gap between the membrane and the sealing rib, thereby opening the fluid path between the medical delivery device and the open top of the container.

10. The resealable container assembly of claim 8, wherein said sealing rib comprises a rib having a square cross-section.

11. The resealable container assembly of claim 8, wherein said sealing rib comprises a rib having a peaked cross-section.

12. The resealable container assembly of claim 8, wherein said sealing rib comprises a rib having a rounded cross-section.

13. The resealable container assembly of claim 1, wherein said body and said means for communicating are formed as a unitary component.

14. The resealable container assembly of claim 1, wherein said body and said top surface are formed as a unitary component.

15. The resealable container assembly of claim 14, wherein said membrane comprises an elastomeric element supported between said body and the top surface of the bottle.

16. The reseatable container assembly of claim 1, wherein said membrane comprises an elastomeric element.

17. The reseatable container assembly of claim 1, wherein said membrane comprises an elastomeric element supported between said body and the top surface of the container.

18. The resealable container assembly of claim 1, further comprising a plurality of sealing ribs disposed about at least a portion of the periphery of said opposed end of the means for communicating for sealing contact with said membrane in the closed position.

19. The resealable container assembly of claim 1, further comprising a sealing rib disposed on said membrane for contact with said body outside of the periphery of the opposed end of the means for communicating.

20. The resealable container assembly of claim 1, wherein the container comprises an annular rim disposed about the open top of the container, said annular rim defining said top surface.

21. The resealable container assembly of claim 20, further comprising a crimp cap for securing said body to said annular rim.

22. The resealable container assembly of claim 1, wherein said at least one fluid passage comprises an opening.

23. The resealable container assembly of claim 1, wherein said body comprises a portion insertable through the open top of the bottle, said membrane comprising an elastomeric element extended across the opposed end of the means for communicating and the open top of the bottle.

24. A resealable container assembly accessible by a medical delivery device and providing a resealable fluid path between the medical delivery device and the container, comprising:

a bottle having an open top and a top surface disposed around portions of the container surrounding said open top;

a body disposed adjacent the top surface of the container;

a luer connector hub for communicating fluids with the container, said luer connector hub having a connector end configured for introduction of the medical delivery device and an opposed end disposed on said body, a plurality of ribs provided about the periphery of the opposed end; and a membrane disposed between the open top of said container and the opposed end of the means for communicating, said membrane having a central area disposed for contact with the medical delivery device and having a width at least equal to the width defined by the opposed end of the means for communicating, said membrane having at least one fluid passage located outside said central area for fluid communication between the medical delivery device introduced into the luer connector hub and the open top of the container, and said membrane defining a sealing portion between said central area and said at least one fluid passage for sealing contact with the plurality of ribs provided on the opposed end of the luer connector hub, wherein upon contact between said medical delivery device and the central area, said membrane is displaced to an open position, wherein said membrane is urged away from sealing contact with the body to open the fluid path between the medical delivery device and the container.

25. A resealable container assembly accessible by a medical delivery device and providing a resealable fluid path between the medical delivery device and the container, comprising:

a bottle having an open top and a top surface disposed around portions of the container surrounding said open top;

a body disposed adjacent the top surface of the container;

a luer connector hub for communicating fluids with the container, said luer connector hub having a connector end configured for introduction of the medical delivery device and an opposed end disposed on said body; and a membrane disposed between the open top of said container and the opposed end of the means for communicating, said membrane having a central area disposed for contact with the medical delivery device and having a width at least equal to the width defined by the opposed end of the means for communicating, said membrane having at least one fluid passage located outside said central area for fluid communication between the medical delivery device introduced into the luer connector hub and the open top of the container, and said membrane defining a plurality of sealing ribs between said central area and said at least one fluid passage for sealing contact with the body, wherein upon contact between said medical delivery device and the central area, said membrane is displaced to an open position, wherein the plurality of sealing ribs of said membrane are urged away from sealing contact with the body to open the fluid path between the medical delivery device and the container.

* * * * *